(12) United States Patent
Peffly et al.

(10) Patent No.: US 7,001,594 B1
(45) Date of Patent: Feb. 21, 2006

(54) SCALP COSMETIC COMPOSITIONS AND CORRESPONDING METHODS OF APPLICATION TO PROVIDE SCALP MOISTURIZATION AND SKIN ACTIVE BENEFITS

(75) Inventors: Marjorie Mossman Peffly, Cincinnati, OH (US); Anthony Raymond Marchetta, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 376 days.

(21) Appl. No.: 09/685,850

(22) Filed: Oct. 10, 2000

(51) Int. Cl.
*A61K 7/06* (2006.01)

(52) U.S. Cl. ............... 424/70.1; 424/400; 424/401; 132/109; 132/108

(58) Field of Classification Search ........... 424/70.1, 424/401, 400; 132/109, 108
See application file for complete search history.

(56) References Cited

U.S. PATENT DOCUMENTS

| | | | |
|---|---|---|---|
| 1,435,911 A | 11/1922 | Bechtold | |
| 2,478,648 A | 8/1949 | Wheeler | |
| 2,624,348 A | 1/1953 | Matson | |
| 3,312,583 A | 4/1967 | Rochlis | |
| 3,950,532 A | 4/1976 | Bouillon et al. | 424/275 |
| 4,170,229 A | 10/1979 | Olson | 128/67 |
| 4,185,099 A | 1/1980 | Sorbini | 424/238 |
| 4,316,887 A | 2/1982 | Kamishita et al. | 424/81 |
| 4,720,046 A | 1/1988 | Morane | |
| 4,728,667 A | 3/1988 | Yanagi et al. | |
| 4,834,076 A | 5/1989 | Millet et al. | 128/65 |
| 4,940,578 A * | 7/1990 | Yoshihara et al. | 424/70 |
| 5,002,075 A * | 3/1991 | Kellett et al. | 132/108 |
| 5,325,878 A * | 7/1994 | McKay | 132/109 |
| 5,523,078 A | 6/1996 | Baylin | 424/70.1 |
| 5,565,207 A * | 10/1996 | Kashibuchi et al. | 424/401 |
| 5,696,169 A | 9/1997 | Otsu et al. | |
| 5,783,202 A | 7/1998 | Tomlinson et al. | |
| 5,997,893 A * | 12/1999 | Jampani et al. | 424/405 |
| 6,588,964 B1 | 7/2003 | Au et al. | |

FOREIGN PATENT DOCUMENTS

| | | |
|---|---|---|
| CA | 959762 | 12/1974 |
| CH | 173913 A | 12/1934 |
| DE | 869247 C | 3/1953 |
| DE | 049493 | 4/1972 |
| DE | 2262376 A | 8/1974 |
| DE | 2322712 | 11/1974 |
| DE | 2438534 | 2/1976 |
| DE | 2452021 | 5/1976 |
| FR | 3203 | 3/1965 |
| FR | 2393570 | 6/1977 |
| FR | 2799621 A1 * | 4/2001 |
| GB | 874368 | 8/1961 |
| GB | 1237656 | 6/1971 |
| GB | 2235380 A | 3/1991 |
| JP | 56110607 | 9/1981 |
| JP | 61-238718 | 10/1986 |
| JP | 01135711 | 5/1989 |
| JP | 03141213 A2 | 6/1991 |
| JP | 07112924 A | 5/1995 |
| JP | 07157415 | 6/1995 |
| JP | 10273422 | 10/1998 |
| JP | 10273423 | 10/1998 |
| JP | 10273424 | 10/1998 |
| JP | 11269043 A | 10/1999 |
| JP | 11302133 | 11/1999 |
| JP | 11322545 | 11/1999 |
| NL | 730966 | 1/1975 |
| SU | 912168 | 7/1980 |
| WO | WO-98/51185 A1 | 11/1998 |
| WO | WO-02/07685 A2 | 1/2002 |
| WO | WO 0232381 A2 | 4/2002 |
| ZA | 680962 | 11/1968 |

* cited by examiner

*Primary Examiner*—Thurman K. Page
*Assistant Examiner*—Lakshmi Channavajjala
(74) *Attorney, Agent, or Firm*—Michael J. Sambrook; Brian M. Bolam; Brent M. Peebles

(57) ABSTRACT

Disclosed are topical leave-on cosmetic compositions, including packaged leave-on compositions, for direct application to the scalp, comprising a) from about 40% to about 99% by weight of a volatile liquid, b) from about 0.005% to about 20% by weight of a skin active agent, and c) from about 0.1% to about 20% by weight of a moisturizing material, preferably a liquid humectant. The composition is a leave-on formulation that is substantially free of cleansing surfactants and is applied directly to the scalp. Also disclosed are methods of treating the scalp by directly applying the topical composition to the scalp. It has been found that the compositions and methods of the present invention can provide improved scalp moisturization and improved deposition of an anti-dandruff or other skin active agent on the skin, without unduly affecting hair cosmetics.

61 Claims, No Drawings

US 7,001,594 B1

SCALP COSMETIC COMPOSITIONS AND CORRESPONDING METHODS OF APPLICATION TO PROVIDE SCALP MOISTURIZATION AND SKIN ACTIVE BENEFITS

FIELD OF INVENTION

The present invention relates to a moisturizing scalp cosmetics and corresponding methods of applying the cosmetics, which contain a skin active agent, directly to the scalp to provided improved moisturization and skin active benefits.

BACKGROUND OF THE INVENTION

Anti-dandruff products are well known and commonly available in the consumer market. Many of these products come in the form of shampoos or hair tonics which contain anti-dandruff ingredients such as zinc pyrithione, triclosan, triclorocarbanalide, dipotassium glycyrrhizinate, monoammonium glycyrrhizinate, allantoin, sulfur-containing materials, isopropylmethylphenol, salicylic acid, and similar other materials.

Anti-dandruff hair and scalp tonics are especially useful in that the consumer can use the anti-dandruff tonic for the desired anti-dandruff effect, but then also select a shampoo tailored to their type of hair care need rather than their need to control or treat dandruff. The net result is good hair cosmetics and control over the flaking and itching associated with dandruff hair. These anti-dandruff tonics are often aqueous liquids that an anti-dandruff active dissolved or dispersed in an aqueous carrier comprising water and up to 80% by weight of small chain alcohol carrier liquids.

Many of the anti-dandruff hair and scalp tonics, however, tend to cause the scalp to become excessively dry, thus countering to some extent the anti-dandruff effect of the anti-dandruff active in the tonic. These tonics often contain a high percentage of volatile carriers such as ethanol that provide the scalp with a cool feeling during and after application, but also tend to dry out the skin, especially after repeated use. These tonics also have the additional problem of contacting the hair during application, and in some cases having a negative impact on hair cosmetics as a result.

It has now been found that hair and scalp tonics containing anti-dandruff or other skin active agents, hereinafter referred to as scalp cosmetic compositions, can be formulated and applied to the scalp without causing the scalp to become excessively dry and without unduly affecting hair cosmetics. This is accomplished by formulating a leave-on composition comprising from about 0.1% to about 20% by weight of a moisturizing material, preferably a liquid humectant, from about 0.005% to about 20% by weight of an anti-dandruff or other skin active agent, and from about 40% to about 99% by weight of a volatile liquid, wherein the composition is substantially free of cleansing surfactants and is applied directly to the scalp.

It has also been found that the scalp cosmetic compositions of the present invention can be applied directly to the scalp to provide not only improved skin moisturization but also improved deposition of the skin active agent on the scalp. The composition is preferably applied directly to the scalp using an applicator or other delivery system having a plurality of openings through which the composition is applied directly to the scalp. This direct application of the composition to the scalp can be accomplished, especially using a suitable applicator or other delivery system, without unduly affecting hair cosmetics.

It is therefore an object of the present invention to provide a composition and method for providing improved delivery of skin active agents to the scalp without unduly affecting hair cosmetics. It is a further object of the present invention to achieve such skin active delivery while also providing improved moisturization to the scalp, especially when the skin active agent is an anti-dandruff material. It is a further objective of the present invention to deliver all such compositions to the desired areas of the scalp by direct application of a leave-on formulation containing a volatile liquid, an anti-dandruff or other skin active agent, and a liquid humectant.

SUMMARY OF THE INVENTION

The present invention is directed to a leave-on scalp cosmetic composition and corresponding methods of applying the composition directly to the scalp, wherein the composition comprises from about 0.1% to about 20% by weight of a moisturizing material, preferably a liquid humectant, from about 0.005% to about 20% by weight of an anti-dandruff or other skin active agent, and from about 40% to about 99% by weight of a volatile liquid, and wherein the composition is substantially free of cleansing surfactants and is applied directly to the scalp. The leave-on scalp cosmetic composition is preferably contained within or by a package having a plurality of openings through which the leave-on scalp cosmetic composition is applied directly to the scalp.

It has been found that the leave-on scalp cosmetic compositions and corresponding methods of the present invention can provide scalp moisturization, anti-dandruff or other skin active benefits, and improved deposition of the skin active agent on the scalp, without unduly affecting hair cosmetics.

DETAILED DESCRIPTION OF THE INVENTION

The scalp cosmetic compositions and corresponding methods of the present invention are directed to the following essential limitations: 1) a volatile liquid carrier, 2) an anti-dandruff or other skin active agent, 3) a moisturizing material, preferably a liquid humectant, and 4) direct application of the composition to the scalp. Each of these limitations will be described in greater detail hereinafter.

The term "volatile" as used herein, unless otherwise specified, refers to those materials that are liquid under ambient conditions and have a vapor pressure as measured at 25° C. that is greater than the vapor pressure of water at 25° C., preferably a vapor pressure greater than about 25 mmHg, more typically a vapor pressure greater than about 35 mmHg. Conversely, the term "nonvolatile" as used herein, unless otherwise specified, refers to those solid or liquid materials that have a vapor pressure as measured at 25° C. that is equal to or less than that of water, i.e., equal to or less than 23.7 mmHg at 25° C.

The term "leave-on" as used herein refers to the composition of the present invention and means that the composition is applied to the desired area of the skin without subsequently rinsing or shampooing the applied area for a period of at least about one hour after application, more typically for a period of at least about 6 hours after application. The term "leave-on" specifically excludes compositions such as shampoos, skin cleansing compositions, and other similar compositions that are applied to the desired area of the body and then immediately rinsed away, or rinsed away within several minutes after application.

The term "ambient conditions" as used herein refers to surrounding conditions at about one atmosphere of pressure (1 atm), at about 50% relative humidity, and at about 25° C., unless otherwise specified. All values, amounts and measurements described herein are obtained under ambient conditions unless otherwise specified.

The scalp cosmetic compositions of the present invention are substantially free of cleansing surfactants. In this context, the term "substantially free" means that the scalp cosmetic composition contains less than 5%, preferably less than 2%, by weight of a cleansing surfactant. It is understood, however, that the composition may contain less than 5% by weight of such surfactants provided that such surfactants are used to stabilize the formulation or to otherwise improve the non-cleansing performance of the composition.

The scalp cosmetic compositions of the present invention are applied directly to the scalp. In this context, the "direct application" means that the composition is applied to primarily to the scalp rather than to the hair, preferably by an applicator or other packaging system having a plurality of openings through which the composition is applied from the applicator or packaging system directly to the scalp rather than the hair. The direct application will typically involve application to both the scalp and that part of the hair or hair shaft nearest or proximal to the scalp, but preferably specifically excludes conventional tonic or shampoo-like application of the composition to the hair and scalp by applying product to the hair and scalp using the hands or other soft substrate, and then massaging the composition through the hair to the desire area of the scalp.

The scalp cosmetic compositions and corresponding methods of the present invention, can comprise, consist of, or consist essentially of the essential elements and limitations of the invention described herein, as well as any of the additional or optional ingredients, components, or limitations described herein or otherwise effective for such use.

All percentages, parts and ratios as used herein are by weight of the total scalp tonic composition, unless otherwise specified. All such weights as they pertain to listed ingredients are based on the specific ingredient level and, therefore, do not include solvents, carriers, by-products, filler or other minor ingredients that may be included in commercially available materials, unless otherwise specified.

Skin Active Agent

The scalp cosmetic compositions of the present invention comprise an anti-dandruff or other skin active agent in an amount sufficient to provide the desired skin active effect. Any anti-dandruff or other skin active agent that is known or otherwise effective in providing anti-dandruff or other skin active effects is suitable for use in the compositions and methods of the present invention. The skin active agent or agents within the composition may be in the form of a solubilized or dispersed liquid, or in the form of a solubilized or dispersed solid.

The skin active agent in the scalp cosmetic compositions and methods of the present invention are formulated with the composition at a variety of concentrations, but will generally represent from about 0.005% to about 20%, more typically from about 0.01% to about 10%, even more typically from about 0.05% to about 7%, by weight of the scalp cosmetic composition. The concentration will vary depending upon factors such as the established safe and effective concentrations for the particular skin active agent selected, the degree or type of skin active benefit sought, and so forth. Non limiting examples of skin active agents suitable for use in the composition include anti-dandruff actives, steroidal anti-inflammatory agents (e.g., hydrocortisone), non-steroidal anti-inflammatory agents, anti-irritation actives, pediculocides or insecticides (e.g. for control of lice, fleas, ticks or other insects), vegetable based phytosterols and their Derivatives (e.g., beta-sitosterol, campesterol, stigmasterol), cooling or other skin sensates, antimicrobial agents other than anti-dandruff actives, anesthetics, anti-histamines, astringents, enzymes, vitamins, hair growth actives, sunscreens, and other similar known or otherwise effective topical pharmaceutical or non-pharmaceutical active.

Non-limiting examples of pediculocides for use as skin active agents include peperonyl butoxide, pyrethrum extract, imidacloprid topical solution, lindane (gammabenzene hexachloride), organophosphates (malathion), natural pyrethrins, synthetic pyrethroids (e.g., permethrin) and any other known or otherwise effective agent for controlling or treating skin, hair or fur against insects such as fleas, lice and other insects.

Non-limiting examples of skin active enzymes for use herein include oxidoreductases, transferases, lyases, hydrolases, isomerases, ligases, and similar other enzymes.

The skin active agent can include selected soothing anti-inflammatory actives at concentrations ranging from about 0.01% to about 5.0%, more preferably from about 0.05% to about 3.0%, by weight of the scalp cosmetic composition. In this context, the soothing anti-inflammatory actives refer to any material other than steroidal anti-inflammatory agents that help to sooth and reduce skin irritation. Non-limiting examples of such actives include pantothenic acid derivatives, pantothenic ether, allantoin, or combinations thereof, preferably an alcohol derivative of pantothenic acid such as panthenol (including d-panthenol and l-panthenol), some examples of which are described in *CTFA Cosmetic Ingredient Handbook*, The Cosmetic, Toiletry and Fragrance Association. Inc. pp. 272–273, 1992, which description is incorporated herein by reference. Panthenol can also be used as a humectant, and shall be considered as a humectant for purposes of defining the compositions of the present invention when such compositions have no other humectants present. Especially preferred are allantoin, Vitamin E oil, and combinations thereof.

The skin active agent is preferably an anti-dandruff active, most typically an antimicrobial anti-dandruff active, concentrations of which within the compositions range from about 0.001% to about 5%, more preferably from about 0.01% to about 3%, even more preferably from about 0.05% to about 1%, by weight of the composition. Preferred antimicrobial anti-dandruff actives include antifungal actives such as pyrithione salts, octopirox, ketoconazole, climbazole, ciclopirox, terbinafine, itraconazole and sulfur or sulfur-containing actives such as selenium sulfide. Most preferred is zinc pyrithione (ZPT) at concentrations ranging from 0.005% to 2%, more preferably from about 0.005% to about 0.5%, by weight of the composition.

Selenium sulfide is a preferred antimicrobial anti-dandruff active for use in the compositions, effective concentrations of which range from about 0.001% to about 5.0%, preferably from about 0.01% to about 2.5%, more preferably from about 0.05% to about 1.0%, by weight of the scalp cosmetic compositions. Selenium sulfide is generally regarded as a compound having one mole of selenium and two moles of sulfur, although it may also be a cyclic structure, $Se_xS_y$, wherein x+y=8. Selenium sulfides are well known in the personal care arts and are described, for example, in U.S. Pat. No. 2,694,668; U.S. Pat. No. 3,152,046; U.S. Pat. No. 4,089,945; and U.S. Pat. No. 4,885,107, which descriptions are incorporated herein by reference.

Other sulfur or sulfur-containing materials may also be used as the antimicrobial active in the scalp cosmetic compositions, concentrations of which generally range from about 0.001% to about 5.0%, preferably from about 0.1% to about 5.0%, more preferably from about 1.0% to about 5.0%, by weight of the scalp cosmetic composition.

Pyrithione antimicrobial actives, especially 1-hydroxy-2-pyridinethione salts, are highly preferred anti-dandruff actives for use in the scalp cosmetic compositions. Preferred pyrithione salts are those formed from heavy metals such as zinc, tin, cadmium, magnesium, aluminum and zirconium. Zinc salts are most preferred, especially the zinc salt of 1-hydroxy-2-pyrithione (zinc pyrithione, ZPT). Other cations such as sodium may also be suitable. Particularly preferred are 1-hydroxy-2-pyrithione salts in platelet particle form, wherein the particles have an average size of up to about 20 microns, preferably up to about 8 microns, most preferably up to about 5 microns. Pyrithione antimicrobial active are well known in the hair care art and are described, for example, in U.S. Pat. No. 2,809,971; U.S. Pat. No. 3,236,733; U.S. Pat. No. 3,753,196; U.S. Pat. No. 3,761,418; U.S. Pat. No. 4,345,080; U.S. Pat. No. 4,323,683; U.S. Pat. No. 4,379,753; and U.S. Pat. No. 4,470,982, which descriptions are incorporated herein by reference.

Other specific examples of zinc-containing skin active agents for use in the compositions and methods of the present invention include zinc pyrithione, zinc acetate, zinc acetylmethionate, zinc aspartate, zinc borate, zinc carbonate, zinc chloride, zinc citrate, zinc DNA, zinc formaldehyde sulfoxylate, zinc gluconate, zinc glutamate, zinc hydrolyzed collagen, zinc lactate, zinc laurate, zinc myristate, zinc neodecanoate, zinc palmitate, zinc PCA, zinc pentadecene tricarboxylate, zinc ricinoleate, zinc ricinoleate, zinc rosinate, zinc stearate, zinc sulfate, zinc undecylenate, zinc oxide, zinc lactobionate, and combinations thereof.

The skin active agent for use in the composition and methods of the of the present invention can include any material that when added to the composition provides hair growth regulation (also referred to herein as "hair growth actives"). In this context, the term "hair growth regulation" includes stimulating hair growth; stimulating hair thickening; preventing, reducing, arresting and/or retarding the loss of hair; preventing, reducing, arresting and/or retarding the thinning of hair; increasing the rate of hair growth; inducing the formation of a greater number of hair strands; increasing the diameter of the hair strand; lengthening the hair strand; changing the hair follicle from vellus follicle to terminal follicle; inducing the formation of vellus follicles; converting follicles from telogen to anagen phase (thereby increasing the overall ratio of anagen phase follicles relative to telogen phase follicles); advancing a follicle from an earlier stage of anagen to a later stage of anagen; reducing the conversion from anagen to catagen phase; treating alopecia; and any combination thereof.

Preferred hair growth actives include zinc-containing salts such as those described herein, especially zinc lactobionate. Other hair growth actives suitable for use in the compositions and methods of the present invention include those described in U.S. Pat. No. 6,124,362 (Bradbury et al.), which description is incorporated herein by reference.

Volatile Liquid

The scalp cosmetic compositions of the present invention comprise a volatile liquid carrier suitable for topical application to human skin. These liquid carriers include any liquid that is volatile under ambient conditions, or any combination of liquid carriers which combination is volatile under ambient conditions, and which is otherwise suitable for topical application to the scalp or other area of the skin.

The volatile liquid carrier or combination of carriers in the scalp tonic compositions of the present invention represent from about 40% to about 99%, preferably from about 50% to about 80%, more preferably from about 55% to about 80%, and even more preferably from about 60% to about 75%, by weight of the scalp cosmetic composition.

The volatile liquid carrier preferably comprises a monohydric alcohol having from 2 to 8 carbon atoms, more preferably from about 2 to 4 carbon atoms, preferred examples of which include ethanol, isopropanol, propanol, n-butanol, t-butanol, isobutanol, and combinations thereof. Most preferred is ethanol. Other volatile liquid carriers can also be used in the composition, preferably non-silicone-containing liquid carriers, either alone or in various combinations such as in combination with the preferred monohydric alcohols described herein. Non-limiting examples of such other volatile liquid carriers include volatile hydrocarbon liquids, polyhydric alcohols, esters or ethers of monohydric or polyhydric alcohols, silicones, and so forth, provided that such other volatile liquid carrier has the requisite volatility as described herein, and provided that such other volatile liquid carrier is not also the liquid humectant component of the composition as described hereinafter.

Moisturizing Material

The scalp cosmetic compositions of the present invention comprise one or more moisturizing materials to provide the composition with improved moisturization and/or flake reduction benefits. The moisturizing material can be any material known or otherwise effective in providing skin moisturization and is preferably limited to those materials that provide the composition with the Scalp Moisturization or Instant Flake Reduction values as described herein.

The moisturizing material for use in the scalp cosmetic compositions of the present invention is preferably a liquid humectant. Suitable humectants include any liquid hygroscopic material that is known for or otherwise effective in providing skin moisturization from a leave-on composition. Concentrations of such materials will vary depending factors such as the formulation selected and the particular humectant within the formulation, but such concentrations will most typically range from about 0.1% to about 20%, more typically from about 0.5% to about 15%, most preferably from about 1.0% to about 10%, by weight of the scalp cosmetic composition.

Liquid humectants suitable for use in the cosmetic scalp compositions of the present invention include any hygroscopic, water soluble liquid having a solubility of at least 50% by weight in water at 25° C. Many of these humectants will have one or more hydroxyl groups attached, non limiting examples of which include liquid polyalkylene glycols such as polypropylene glycols and diethylene or polyethylene glycols (e.g., molecular weights from about 200 to about 600, such as PEG-4, PEG-6, PEG-8. PEG-12) ethyl hexanediol, hexylene glycol, butylene glycol, glycerin, propylene glycol, dipropylene glycol, tripropylene glycol, polypropylene-5-laureth-5, polyglycerol cocoate, sorbitol, fructose, glycine, inositol, panthenol and combinations thereof.

Specific non-limiting examples of suitable humectants include Lubrajel Oil® (glyceryl polymethacrylate and propylene glycol), Glucquat® 125 (lauryl methyl gluceth-10 hydroxypropyldimonium chloride), Glucam® E-10 (methyl gluceth-10), Glucam® E-20 (methyl gluceth-20), Glucam® P-10 (PPG-10 methyl glucose ether), Glucam® P-20 (PPG-20 methyl glucose ether), sodium lactate, sodium PCA, Schercomid LME (Lactamide MEA), Clearcol (soluble collagen), Collasol M (soluble collagen), Crolastin (hydrolyzed elastin), Cromoist CS (sodium chrondroitin sulfate and hydrolyzed collagen), Cromoist HYA (hydrolyzed collagen and hyaluronic acid), Cromoist WHYA (hydrolyzed wheat protein and hylauronic acid), Cromoist O-25 (hydrolyzed oats), Cropeptide W (hydrolyzed wheat protein and hydrolyzed wheat starch), Crosilk 10,000 (hydrolyzed silk), Crosilk Liquid (silk amino acids), Crosilkquat (Cocodimonium hydroxypropyl silk amino acids), Crotein CAA/SF (collagen amino acids), Crotein HKP (hair keatin amino acids and sodium chloride, Crotein HKP/SF (keratin amino acids), Crotein MCAA (collagen amino acids), Hydrolactin 2500 (hydrolyzed milk protein), Hydrosoy 2000 (hydrolyzed soy protein), Hydrotriticum™ 2000 (hydrolyzed wheat protein), Hydrotriticum™ WAA (wheat amino acids), Reticusol (hydrolyzed reticulin), Tritisol™ (hydrolyzed wheat protein), Incromectant AMEA-100 (acetamide MEA), Incromectant AMEA-70 (acetamide MEA), Incromectant LMEA (acetmide MEA and lactamide MEA), Incromectant AQ (acetamidopropyl trimonium chloride), Incromectant LQ (lactamidopropyl trimonium chloride), Gelatin NF, Lactil® (sodium lactate and sodium PCA, and glycine and fructose and urea and niacinamide and inocitol, and sodium benzoate and lactic acid).

The humectant for use in the cosmetic scalp composition preferably penetrates the upper layers of skin of the scalp, i.e., the stratum corneum layer, and then draws moisture into those skin layers, thus providing improved moisturization of the scalp after application. The humectant preferably helps provide the composition with the preferred skin moisturization measurements as defined hereinafter.

Product Form

The scalp cosmetic composition of the present invention is a flowable liquid under ambient conditions and has a viscosity of from about 20 centistokes to about 60,000 centistokes, preferably from about 100 to about 20,000 centistokes. These flowable liquids can be in a variety of forms, including dispersions, multi-phase emulsions or suspensions, or single phase solutions.

It has been found that the scalp cosmetic compositions should have a product viscosity under ambient or use conditions within the ranges recited herein to provide the acceptable spreading when applied directly to the scalp, especially when applied directly to the scalp from an applicator or other packaging system designed for direct scalp application. It has also been found that scalp cosmetic compositions with zinc-containing anti-dandruff actives should have a minimum viscosity of at least 1,000 centistokes, preferably from about 1,000 to about 20,000 centistokes, to provide the desired spreading during application and to provide a uniform distribution of the zinc-containing active on the applied areas of the scalp.

Product Characteristics

The scalp cosmetic compositions and methods of the present invention provide benefits to the scalp such as itch relief, irritation relief, moisturization, reduced flaking, reduced drying times on the scalp, and other benefits associated with the particular skin active agent selected. Such other benefits could include, depending upon the active selected, hair growth (e.g., ZPT or other hair growth active), dandruff control or inhibition, anti-inflammation, anti-fungal or other anti-microbial effects, and so forth.

The scalp cosmetic compositions of the present invention preferably provide one or more of the following performance characteristics, which includes Flake Reduction and Scalp Moisturization values as defined herein, which characteristics are helpful in providing the product benefits described hereinbefore. These performance characteristics are determined in accordance with the methodologies as defined hereinafter.

1. Initial Flake Reduction

The scalp cosmetic compositions and methods of the present invention provide improved moisturization and flake reduction of the scalp, especially on those applied areas of the scalp that are being treated for dandruff control or elimination. The compositions are especially effective in providing both short term flake reduction as a result of scalp moisturization, as well as long term flake reduction as a result of continued product application and control of scalp conditions that cause flaking, e.g., dandruff control through continued application and improved deposition of anti-dandruff actives.

The scalp cosmetic compositions preferably provide initial flake reduction as measured five (5) minutes after application to provide an Initial Flake Reduction value as defined herein that is preferably at least about 40%, more preferably at least about 50%, flake reduction. The Initial Flake Reduction is essentially a measure of the percentage of visible flakes reduced over a given area as a result of the cosmetic application to that area. This Initial Flake Reduction is a measure that correlates with the effectiveness of the composition to moisturize the scalp and reduce the appearance of visible flaking shortly after application or treatment. The Instant Flake Reduction value is determined according to the following methodology.

In accordance with the Instant Flake Reduction methodology, each panelist washes their legs during normal bathing sessions for 3 days prior to start of panel; no moisturizers of creams of any sort are used on the legs during the wash-out period. Several 3×7 cm areas are then marked off on each leg using a sharpie marker. The cosmetic scalp composition (0.1 ml from a syringe) is applied topically to one of the marked areas and spread evenly over the entire area using a latex gloved finger. One of the marked areas on each panelist is kept as a control where no product is applied. Five minutes after application, a D-Squame® disc (standard 22 mm clear disc, available from CUDerm Corporation, Dallas, Tex., U.S.A) [is pressed against the treated area and then immediately removed and then pressed against and onto a D-squame storage card. This step involving the D-squame disc is repeated using the control (non treated) area of skin as well. Flaking is observed on the D-squame disc for the treated and untreated areas, and the Instant Flake Reduction value is determined as the percent reduction in the number of flakes on the disk relative to the untreated control.

2. Scalp Moisturization

The scalp cosmetic compositions of the present invention comprises a moisturizing material, preferably a humectant, as described hereinbefore, wherein the moisturizing material helps provide the composition with the ability to moisturize the scalp and help reduce flaking and/or itching resulting from dry or irritated skin. The scalp moisturization provided by the scalp cosmetic compositions can be characterized by a measured skin moisture content at approximately 4.0 hours after application of the composition to the scalp.

Scalp moisturization for purposes of characterizing the compositions and methods of the present invention can be indirectly determined by measuring skin moisturization on the legs after application of the scalp cosmetic composition to the legs. This skin moisturization measurement is determined by the following methodology. All readings described hereinafter are obtained at 23° C. and 50% relative humidity.

In accordance with the moisturization measurement methodology herein, each of the panelist first washes their legs during normal bathing sessions for 3 days prior to start of panel; no moisturizers or creams are used on the legs during the wash-out period. Several 3×7 cm areas are marked on each leg using a sharpie marker. Prior to any product treatment, Skicon readings are taken (Skicon-200, available from I.B.S. Co. Ltd. (Shizuoka-ken, Japan) at five different points within a marked area prior to any product application. The Skicon is used to evaluate skin surface hydration by measuring conductance (micro ohms or $\mu\sigma$) using a multi-point probe to avoid hair and insure contact with the stratum corneum. The five Skicon readings prior to product treatment are averaged as a baseline against which Skicon readings from treated skin will be compared.

After obtaining the baseline reading, 0.1 ml of the product is applied to the area on which the baseline readings were obtained and spread evenly over the entire area using a latex gloved finger. One of the marked areas is designated as a control on which no product is applied during testing. Four (4) hours after application, five more Skicon readings are taken on within the applied and marked area. These four (4) readings are averaged. The averaged baseline read is then subtracted from the average four (4 0 hour reading for the same applied area to get the increase in moisturization that can be attributed to the application of the product on that area. This increase in moisturization is then compared to the increase in moisturization measured on the untreated control over the same four (4) hour period. This increase in skin moisturization of treated skin to untreated skin on the leg, correlates with the increase in skin moisturization that would also be expected for similar product application on the scalp. This relative increase in moisturization of treated to untreated skin is characterized herein as the Scalp Moisturization value, and is the ratio of the moisturization increase of the treated to untreated skin.

The scalp cosmetic compositions and methods of the present invention preferably provide a Scalp Moisturization value of at least about 2.5, more preferably at least about 4.0, even more preferably at least about 6.0, most typically within the range of from about 2.5 to about 10.0.

Application System

The scalp cosmetic composition of the present invention is applied directly to the scalp to reduce initial contact with the hair and to improve deposition of the skin active agent on the scalp. Any known or otherwise effective method or application system for directly applying the product to the scalp is suitable for use in the compositions and methods of the present invention.

The scalp cosmetic compositions of the present invention are applied directly to the scalp. In this context, direct application of the composition means that it is applied primarily to the scalp rather than to the hair, preferably by an applicator or other packaging system having a plurality of openings through which the composition is applied from the applicator or packaging system directly to the scalp rather than the hair. The direct application will typically involve application to both the scalp and that part of the hair or hair shaft nearest or proximal to the scalp, but preferably specifically excludes conventional tonic or shampoo-like application of the composition to the hair and scalp by applying product to the hair and scalp using the hands or other soft substrate, and then massaging the composition through the hair to the desire area of the scalp.

The scalp cosmetic composition can be applied directly to the scalp without the use of an applicator or other packaging system, provided that the application is applied directly to the scalp as defined herein. For example, the direct application can be accomplished by carefully applying the scalp cosmetic composition to the finger tips, and then inverting or turning down the head so that the hair hangs away from the scalp, and then carefully and directly applying the product from the finger tips to the exposed scalp areas.

The scalp cosmetic composition is preferably applied directly to the scalp by using an application system comprising an applicator or other packaging system, wherein the application is directed through a plurality of openings that are directed past the hair and directly on or in close approximation to the scalp, such that the application of the composition is applied directly to the scalp, although some product will also contact some of the hair shafts near the scalp surface.

Examples of application systems for use in the compositions and methods of the present invention include any packaging system comprising a reservoir within which the composition is contained or passes through, and a plurality of openings or tines attached or otherwise connect to the reservoir and through which the composition passes away from the reservoir and directly onto the scalp surface. The packaging system preferably contains at least about 3 such openings or tines, more typically from about 3 to about 300 tines, although the number of openings or tines will vary depending upon factors such as the desired applicator size, design, etc. Preferably the openings are located within and at the distal end of the tines, i.e., distal to the reservoir and proximal to the site of application.

Other suitable application systems include packaging or application systems that may or may not contain a composition reservoir, but which comprise a comb or brush that allows for direct application of the composition from the comb or brush to the scalp, e.g., dip part of a comb or brush in the scalp cosmetic composition and apply the brush or comb to the scalp.

Optional Ingredients

The scalp cosmetic compositions of the present invention may further comprise one or more optional components known for use in hair care or personal care products, provided that the optional components are physically and chemically compatible with the essential component described herein, or do not otherwise unduly impair product performance. Concentrations of such optional components most typically and individually range from about 0.001% to about 10% by weight of the scalp cosmetic composition.

Non limiting examples of optional components for use in the scalp cosmetic compositions include dyes, emulsifiers and surfactants, pH adjusting agents, fragrance chemicals and perfumes, preservatives, proteins, sunscreens, vitamins (e.g., vitamin E oil), viscosity adjusting agents, colorants, suspending or thickening agents (e.g., polyacrylate thickeners), and so forth.

Still other optional ingredients include skin sensates, preferably cooling skin sensates, some non-limiting examples of which are described in U.S. Pat. No. 4,230,688 (Rowsell et al.) and U.S. Pat. No. 4,136,163 (Watson et al.), which descriptions are incorporated herein by reference. Non-limiting examples of optional sensates include menthol, methone glycerin acetal, methyl diisopropyl propionamide, menthyl lactate, menthoxy-1,2-propanediol, ethyl carboxamide, trimethyl butanamide, menthyl lactate, butanedioic acid monomenthyl ester, vanillyl butyl ether, 1-isopulegol, cineole, methylsalicylate, eucalyptus oil, carvone, rosemary oil, ginger oil, clove oil, ethyl menthane carboxamide, camphor, eucolytol, peppermint oil, and combinations thereof, concentrations of which preferably range from about 0.01% to about 2.0%, more preferably from about 0.01% to about 1.0%, by weight of the composition.

The scalp cosmetic compositions of the present invention optionally comprise a non-volatile carrier liquid in addition to the volatile carrier liquid as described hereinbefore. The non-volatile carrier can be any liquid carrier that is known or otherwise suitable for application to the scalp, wherein the optional non-volatile carrier at the selected concentration does not unduly impact product performance. The optional non-volatile carrier liquid can be aqueous or non aqueous, silicone-containing or non silicone-containing, but when present is preferably an aqueous carrier that provides the composition with a water concentration of up to about 50%, more preferably from about 5% to about 50%, even more preferably from about 10% to about 40%, by weight of the scalp cosmetic composition. Non limiting examples of non-volatile liquids for optional use herein are described in U.S. Pat. No. 6,074,655 (Fowler et al.) which descriptions are incorporated herein by reference.

Method of Application

The scalp cosmetic composition of the present invention can be applied directly to the scalp such that most of the composition is initially applied directly to the skin rather than to the hair. This is preferably accomplished by applying the composition from a packaging system or delivery system as described herein and comprising a plurality of openings through which the composition can be directed past the hair and directly to the scalp. The composition is applied directly to the scalp in an amount effective to provide the desired moisturization and/or skin active benefit. Application amounts will vary considerably depending upon factors such as the needs of the user and the formulation selected, but will most typically range from about 0.1 grams to about 10 grams per application, more typically from about 0.5 grams to about 5 grams per application, and can be applied one or more times daily to either damp or dry scalp.

The scalp cosmetic composition and methods of the present invention are especially useful when formulated and applied as described herein, except that the composition is applied to any or all areas of the skin or fur of animals such as livestock (e.g., horses, cattle) and domestic pets (e.g., cats and dogs), wherein such areas would benefit from application of the skin active agent onto the skin of the animal.

The methods of the present invention are preferably directed to the application of the compositions described herein, wherein such application is made directly to the scalp or other area of the skin, and is accomplished using the packaging or delivery system described herein. Especially preferred are those method of application embodiments directed to the application of hair growth agents or anti-dandruff actives to the scalp using the applicator system as described herein, especially zinc-containing hair growth actives and zinc-containing anti-dandruff actives from such an applicator, wherein such preferred method of application embodiments include the use of all of the compositions as described herein and any modified compositions thereof which do not contain any humectants or other similar moisturizing materials.

Method of Manufacture

The scalp cosmetic compositions of the present invention may be prepared by any known or otherwise effective technique suitable for combining the essential ingredients of the compositions, and any selected optional ingredients, to form a physically stable, liquid composition suitable for application to the skin.

For example, the scalp cosmetic composition of the present invention can be formulated as an oil in water emulsion, which involves the formulation of both an oil in water emulsion and a Carbopol thickened product neutralized with aminomethyl propanol (AMP).

1. Carbopol Ultrez-10 (polyacrylate polymer, available from B.F. Goodrich) is mixed with deionized water with a medium level of agitation to fully hydrate the powder. Mixing should be continued until the Carbopol looks completely wetted with no agglomerations and has a slightly hazy appearance.
2. Additional ingredients are then be added to the batch prior to thickening with base, preferably any water soluble materials such as the humectants, panthenol, are added. Allantoin is also added at this point.
3. A ZPT premix (or other similar skin active agent premix) is then made with either ethanol or ethanol and water. The ZPT is added to the water, humectant, carbopol mix prior to addition of an oil phase or thickening the carbopol (aqueous phase).
4. In a separate premix, the oil soluble materials (includes Vitamin E acetate, menthyl lactate, menthol, perfume), ethanol, glycol, and emulsifiers are combined to form an oil-ethanol phase.
5. The oil-ethanol phase is added to the aqueous phase with agitation to form a white, milky-appearing emulsion.
6. The milky-appearing emulsion is neutralized with aminomethyl propanol (AMP-regular) using a ration of 0.85 AMP to 1 unit of Carbopol. Generally, the AMP is premixed with a portion of ethanol to achieve better mixing and a faster neutralization rate. Once the neutralizer is added, mixing is continued for about 30 minutes to insure a homogeneous batch representing a cosmetic scalp cosmetic embodiment of the present invention.

EXAMPLES

The following non limiting examples illustrate specific scalp cosmetic embodiments and methods of the present invention. Each of the exemplified compositions is prepared by methods well known in the formulation arts for preparing hydro-alcoholic liquids. All exemplified amounts are weight percents based on the total weight of the scalp cosmetic compositions, unless otherwise specified.

Each of the exemplified compositions is then packaged into a suitable applicator and then applied directly to the scalp or other suitable area of the skin. The composition is not rinsed or otherwise removed from the skin for at least 1–6 hours after application. Each of the exemplified compositions provides the applied area of the scalp with improved deposition of the skin active agent, improved skin or scalp moisturization, without unduly affecting hair cosmetics.

Each of the exemplified compositions is also formulated using skin active agents other than anti-dandruff actives, including steroidal anti-inflammatory agents (e.g., hydrocortisone), non-steroidal anti-inflammatory agents, pediculocides, antimicrobial agents other than anti-dandruff actives, anesthetics, anti-histamines, astringents, enzymes, vitamins, hair growth actives other than ZPT, and sunscreens. Each of these reformulated compositions provides improved moisturization of the skin or scalp and improved deposition of the skin active agent on the skin after direct application.

TABLE 1

Leave-on Scalp Cosmetic Compositions

| Ingredient: | I | II | III | IV | V | VI | VII |
|---|---|---|---|---|---|---|---|
| | Weight % | | | | | | |
| Water, DRO | qs | qs | qs | qs | qs | qs | qs |
| Carbomer (1) | 0.3 | 0.3 | 0.4 | | | — | 0.1 |
| Carbomer (2) | | | | 0.5 | — | | |
| Polyacrylamide (and) C13–14 Isoparaffin (an) Laureth-7 (3) | | | | — | 4.0 | 2.5 | |
| Aminomethyl propanol (4) | 0.26 | 0.285 | 0.34 | — | — | — | 0.13 |
| Tetrahydroxypropyl Ethylenediamine (5) | — | — | — | 0.5 | — | | — |
| Ethanol (6) | 55.0 | 50.0 | 55.0 | 55.0 | 55.0 | 60.0 | 45.0 |
| Zinc Pyrithione (7) | 0.1 | 0.1 | 0.09 | 0.01 | 0.01 | 0.2 | 0.1 |
| Zinc sulfate (8) | — | — | | 0.01 | 0.1 | — | — |
| Zinc lactate (9) | — | — | — | — | — | 0.2 | — |
| Menthyl Lactate (10) | 0..35 | 0.1 | 0.25 | — | 0.5 | — | 0.5 |
| Menthol (11) | 0.15 | 0.1 | 0.25 | 0.25 | 0.25 | 0.25 | 0.5 |
| Menthone Glycerin Acetal (12) | | | | 0.5 | | | |
| Panthenol (13) | 1.0 | 1.0 | 1.0 | 1.0 | 1.0 | 2.0 | 1 |
| Tocopherol Acetate (14) | 0.5 | 1.0 | 1.0 | 1.0 | 1.0 | 2.0 | — |
| PEG-60 Hydrogenated Caster Oil (15) | 1.0 | | 1.0 | 1.0 | | 2.0 | |
| PEG-25 Glycerol Trioleate (16) | — | — | — | — | 1.0 | — | — |
| Hexylene Glycol (17) | — | 1.0 | — | — | — | — | — |
| Glycerin (18) | 5.0 | 5.0 | 5.0 | 5.0 | 5.0 | 4.0 | 3.0 |
| Allantoin (19) | 0.05 | 0.05 | 0.08 | 0.08 | 0.1 | 0.10 | — |
| Isoceteth-20 (70% act.) (20) | 0.71 | | — | 0.1 | 0.1 | 2.0 | — |
| Cetearth-20 (21) | | 0.5 | | | | — | |
| Fragrance (22) | 0.30 | 0.30 | 0.30 | 0.30 | 0.30 | 0.30 | 0.30 |
| Zinc oxide (23) | — | — | .001 | — | .01 | — | — |

(1) Carbopol Ultrez 10, supplier: B. F. Goodrich
(2) Carbopol ETD 2020; supplier: B. F. Goodrich
(3) Sepigel 305, supplier: Seppic
(4) AMP Regular, supplier: Angus
(5) Neutrol TE, supplier: BASF
(6) 200 proof, SDA 40-2
(7) small platlet ZPT (2.5 m), supplier: Arch
(8) Whitco Zinc Stearate D. USP, supplier: Witco
(9) Puramex ZN, supplier: Purac
(10) Frescolate ML, supplier: Haarman & Reimer
(11) USP Menthol, supplier: Haarman & Reimer
(12) Frescolat MGA, supplier: Haarman & Reimer
(13) D Panthenol, supplier: Hoffmann LaRoche
(14) Vitamin E Acetate, supplier: BASF
(15) Cremophor RH 60, supplier: BASF
(16) Tagat TO, supplier: Goldsmidt
(17) Hexylene Glycol, supplier: Van Waters & Rodgers
(18) Superol USP, supplier: Procter & Gamble
(19) Allantoin micronized, supplier: ICI
(20) Arlasolve 200L, supplier ICI
(21) Cremaphor A20, supplier: BASF
(22) Fragrance, supplier Haarman & Reimer
(23) Z-cote HP1, supplier: BASF

TABLE 2

Leave-on Scalp Cosmetic Compositions

| | VIII | IX | X | XI | XII | XIII | XIV | XV |
|---|---|---|---|---|---|---|---|---|
| Water, DRO | qs | qs | qs | qs | qs | qs | qs | qs |
| Carbomer (1) | 0.3 | — | 0.4 | | | — | | 0.1 |
| Carbomer (2) | | .5 | | 0.5 | | — | | |
| Polyacrylamide (and) C13–14 Isoparaffin (an) Laureth-7 (3) | | | | — | 0.5 | 1.0 | | |
| Aminomethyl propanol (4) | 0.26 | — | 0.34 | — | — | — | | 0.13 |
| Tetrahydroxypropyl Ethylenediamine (5) | — | .5 | — | 0.5 | — | | | — |
| Ethanol (6) | 55.0 | 50.0 | 55.0 | 55.0 | 55.0 | 60.0 | | 45.0 |
| Selenium Sulfide (7) | 0.05 | | | | | | | |
| Ketaconazole (8) | | 0.1 | | | | | | |
| Climbazole (9) | — | — | .05 | — | | — | | — |
| Salicylic Acid (10) | — | — | — | 3.0 | — | 0.2 | | — |
| Pyrethrins (11) | | | | | 0.1 | | | |
| Protease, Lipase mixture (12) | | | | | | | | |

TABLE 2-continued

Leave-on Scalp Cosmetic Compositions

|  | VIII | IX | X | XI | XII | XIII | XIV | XV |
|---|---|---|---|---|---|---|---|---|
| Hydrocortisone (13) |  |  |  |  |  | 0.1 |  |  |
| Bacitracin Zinc (14) |  |  |  |  |  |  | 0.1 |  |
| Tolnaftate (15) |  |  |  |  |  |  |  | 1.0 |
| Menthyl Lactate (16) | 0.25 | 0.1 | 0.25 | 0.25 | 0.25 | 0.50 | 0.1 | 0.5 |
| Panthenol (17) | 1.0 | 1.0 | 1.0 | 1.0 | 1.0 | 2.0 | 0.5 | 1.0 |
| Tocopherol Acetate (18) | 0.5 | 1.0 | 1.0 | 1.0 | 1.0 | 2.0 | — | — |
| PEG-60 Hydrogenated Caster Oil (19) | 0.5 | 1.0 | 1.0 | 1.0 | 1.0 | 2.0 | — | — |
| Glycerin (20) | 5.0 | — |  | 3.0 | 5.0 | 10.0 | 1.0 | 3.0 |
| Sorbitol (21) |  | 4.0 | — | — | 1.0 | — |  | — |
| Glyceryl Polymethyacrylate & Propylene Glycol (22) |  |  | 5.0 |  | — | — | 3.0 | — |
| Methyl Glyceth-20 (23) |  |  |  | 1.0 |  | — |  | — |
| Isoceteth-20 (70% act.) (24) | 0.71 | 0.7 | 0.7 | 0.1 | 0.1 | 2.0 | — | — |
| Fragrance (25) | 0.30 | 0.30 | 0.30 | 0.30 | 0.30 | 0.30 |  | 0.30 |

(1) Carbopol Ultrez 10, supplier: B. F. Goodrich
(2) Carbopol ETD 2020; supplier: B. F. Goodrich
(3) Sepigel 305, supplier: Seppic
(4) AMP Regular, supplier: Angus
(5) Neutrol TE, supplier: BASF
(6) 200 proof, SDA 40-2
(7) Selenium Sulfide, USP, supplier: Abbot Labs
(8) Anti-dandruff active
(9) Climbazol, supplier: Bayer AG
(10) Unichem SALAC, supplier: UPI
(11) Anti-lice pesticide
(12) Enzyme mixture for lice treatment
(13) Steroid - anti-itch, anti-inflammation
(14) Bactericide
(15) Fungicide
(16) Frescolate ML, supplier: Haarman & Reimer
(17) D Panthenol, supplier: Hoffmann LaRoche
(18) Vitamin E Acetate, supplier: BASF
(19) Cremophor RH 60, supplier: BASF
(20) Superol USP, supplier: Procter & Gamble
(21) Sorbo 70% Sorbitol solution, supplier: ICI
(22) Lubrajel Oil, supplier ISP
(23) Glucam E-20, supplier: Amerchol
(24) Arlasolve 200L, supplier ICI
(25) Fragrance, supplier Haarman & Reimer

What is claimed is:

1. A scalp cosmetic composition comprising:
  a) from about 40% to about 99% by weight of a volatile liquid having a vapor pressure greater than 23.7 mmHg as measured at 25° C., and
  b) from about 0.005% to about 20% by weight of a skin active agent,
  c) from about 0.1% to about 20% by weight of a liquid humectant,
  wherein the composition is a leave-on composition that is substantially free of cleansing surfactants and wherein the composition is contained within an applicator having a plurality of openings through which the composition is applied directly to the scalp.

2. The composition of claim 1 wherein the skin active agent is an antidandruff active and represents from about 0.005% to about 2% by weight of the composition.

3. The composition of claim 2 wherein the anti-dandruff active is zinc pyrithione.

4. The composition of claim 1 wherein the skin active agent is selected from the group consisting of anti-dandruff actives, steroidal anti-inflammatory agents, non-steroidal anti-inflammatory agents, pediculocides, sensates, enzymes, vitamins, hair growth actives, sunscreens, and combinations thereof.

5. The composition of claim 3 wherein the hair growth active is selected from the group consisting of zinc lactobionate, zinc pyrithione, and combinations thereof.

6. The composition of claim 1 wherein the volatile liquid has a vapor pressure as measured at 25° C. of at least about 25 mmHg.

7. The composition of claim 6 wherein the volatile liquid comprises a monohydric alcohol having from 2 to 8 carbon atoms, wherein the monohydric alcohol represents from 20% to about 100% by weight of the volatile liquid.

8. The composition of claim 7 wherein the monohydric alcohol is ethanol.

9. The composition of claim 1 wherein the composition further comprises from about 5% to about 50% by weight of water.

10. The composition of claim 1 wherein the composition contains less than 2% by weight of a cleansing surfactant.

11. The composition of claim 1 wherein the humectant represents from about 1% to about 10% by weight of the composition.

12. The composition of claim 11 wherein the humectant is selected from the group consisting of polypropylene glycol, polyethylene glycol, ethyl hexanediol, hexylene glycol, glycerin, propylene glycol, sorbitol, and combinations thereof.

13. The composition of claim 1 wherein the composition further comprises from about 0.01% to about 2% by weight of a cooling sensate.

14. The composition of claim 1 wherein the composition provides an Instant Flake Reduction value of at least about 40%.

15. The composition of claim 1 wherein the composition provides an Instant Flake Reduction value of at least about 50%.

16. The composition of claim 1 wherein the composition provides a Scalp Moisturization value of at least about 2.5.

17. The composition of claim 1 wherein the composition provides a Scalp Moisturization value of from about 4.0 to about 10.0.

18. The composition of claim 1 wherein the skin active agent comprises allantoin.

19. The composition of claim 1 wherein the composition further comprises Vitamin E oil.

20. A method of treating the scalp, said method comprising:
   a) applying directly to the scalp a cosmetic composition that is substantially free of cleansing surfactants and which contains:
      i) from about 40% to about 99% by weight of a volatile liquid having a vapor pressure greater than 23.7 mmHg as measured at 25° C., and
      ii) from about 0.005% to about 20% by weight of a skin active agent,
      iii) from about 0.1% to about 20% by weight of a liquid humectant,
   wherein the composition is contained within an applicator having a plurality of openings through which the composition is applied directly to the scalp, and
   b) allowing the applied composition to remain on the scalp for at least about 30 minutes after application.

21. The method of claim 20 wherein the skin active agent is an antidandruff active and represents from about 0.005% to about 2% by weight of the composition.

22. The method of claim 21 wherein the anti-dandruff active is zinc pyrithione.

23. The method of claim 20 wherein the skin active agent is selected from the group consisting of anti-dandruff actives, steroidal anti-inflammatory agents, non-steroidal anti-inflammatory agents, pediculocides, skin sensates, enzymes, vitamins, hair growth actives, sunscreens, and combinations thereof.

24. The method of claim 20 wherein the hair growth active is selected from the group consisting of zinc lactobionate, zinc pyrithione, and combinations thereof.

25. The method of claim 20 wherein the volatile liquid has a vapor pressure as measured at 25° C. of at least about 25 mmHg.

26. The method of claim 25 herein the volatile liquid comprises a monohydric alcohol having from 2 to 8 carbon atoms, wherein the monohydric alcohol represents from 20% to about 100% by weight of the volatile liquid.

27. The method of claim 26 wherein the monohydric alcohol is ethanol.

28. The method of claim 20 wherein the composition further comprises from about 5% to about 50% by weight of water.

29. The method of claim 20 wherein the composition contains less than 2% by weight of a cleansing surfactant.

30. The method of claim 20 wherein the humectant represents from about 1% to about 10% by weight of the composition.

31. The method of claim 30 wherein the humectant is selected from the group consisting of polypropylene glycol, polyethylene glycol, ethyl hexanediol, hexylene glycol, glycerin, propylene glycol, sorbitol, and combinations thereof.

32. The method of claim 20 wherein the composition further comprises from about 0.01% to about 2% by weight of a cooling sensate.

33. The method of claim 20 wherein the composition provides an Instant Flake Reduction value of at least about 40%.

34. The method of claim 20 wherein the composition provides an Instant Flake Reduction value of at least about 50%.

35. The method of claim 20 wherein the composition provides a Scalp Moisturization value of at least about 2.5.

36. The method of claim 20 wherein the composition provides a Scalp Moisturization value of from about 4.0 to about 10.0.

37. The method of claim 20 wherein the skin active agent comprises allantoin.

38. The method of claim 20 wherein the composition further comprises Vitamin E oil.

39. A method of treating animal skin, said method comprising:
   a) applying directly to the scalp a cosmetic composition that is substantially free of cleansing surfactants and which contains:
      i) from about 40% to about 99% by weight of a volatile liquid having a vapor pressure greater than 23.7 mmHg as measured at 25° C., and
      ii) from about 0.005% to about 20% by weight of a skin active agent,
      iii) from about 0.1% to about 20% by weight of a liquid humectant,
   wherein the composition is contained within an applicator having a plurality of openings through which the composition is applied directly to the scalp, and
   b) allowing the applied composition to remain on the scalp for at least about 30 minutes after application.

40. The method of claim 39 wherein the method is directed to animals selected from the group consisting of cattle, horses, dogs, and cats.

41. The method of claim 40 wherein the skin active agent is selected from the group consisting of steroidal anti-inflammatory agents, non-steroidal anti-inflammatory agents, pediculocides, and combinations thereof.

42. The method of claim 41 wherein the skin active agent comprises a pediculocide.

43. The method of claim 42 wherein the method is directed to the control of insects selected from the group consisting of fleas, ticks, lice, and combinations thereof.

44. The method of claim 42 wherein the composition is contained within an applicator having a plurality of openings through which the composition is applied directly to the scalp.

45. A scalp cosmetic composition comprising:
   a) from about 40% to about 99% by weight of a volatile liquid having a vapor pressure greater than 23.7 mmHg as measured at 25° C., and
   b) from about 0.005% to about 20% by weight of a skin active agent,
   c) from about 0.1% to about 20% by weight of a liquid humectant,
   wherein the composition is a leave-on composition that is substantially free of cleansing surfactants and wherein the composition is contained within an applicator having a plurality of openings through which the composition is applied directly to the scalp, and provides a Scalp Moisturization value of at least about 2.5.

46. The composition of claim 45 wherein the skin active agent is an antidandruff active and represents from about 0.005% to about 2% by weight of the composition.

47. The composition of claim 46 wherein the anti-dandruff active is zinc pyrithione.

48. The composition of claim 45 wherein the skin active agent is selected from the group consisting of steroidal anti-inflammatory agents, non-steroidal anti-inflammatory agents, pediculocides, cooling sensates, enzymes, vitamins, hair growth actives, sunscreens, and combinations thereof.

49. The composition of 48 wherein the skin active agent is a hair growth active selected from the group consisting of zinc lactobionate, zinc pyrithione, and combinations thereof.

50. The composition of claim 45 wherein the composition contains less than 2% by weight of a cleansing surfactant.

51. The composition of claim 45 wherein the moisturizing material is a humectant and represents from about 1% to about 10% by weight of the composition.

52. The composition of claim 51 wherein the humectant is selected from the group consisting of polypropylene glycol, polyethylene glycol, ethyl hexanediol, hexylene glycol, glycerin, propylene glycol, sorbitol, and combinations thereof.

53. The composition of claim 45 wherein the composition provides a Scalp Moisturization value of from about 4.0 to about 10.0.

54. A scalp cosmetic composition comprising:
   a) from about 40% to about 99% by weight of a volatile liquid having a vapor pressure greater than 23.7 mmHg as measured at 25° C., and
   b) from about 0.005% to about 20% by weight of a skin active agent,
   c) from about 0.1% to about 20% by weight of a liquid humectant,
   wherein the composition is a leave-on composition that is substantially free of cleansing surfactants and wherein the composition is contained within an applicator having a plurality of openings through which the composition is applied directly to the scalp, and provides an Instant Flake Reduction value of at least about 40%.

55. The composition of claim 54 herein the skin active agent is an antidandruff active and represents from about 0.005% to about 2% by weight of the composition.

56. The composition of claim 55 wherein the anti-dandruff active is zinc pyrithione.

57. The composition of claim 54 wherein the skin active agent is selected from the group consisting of steroidal anti-inflammatory agents, non-steroidal anti-inflammatory agents, pediculocides, cooling sensates, enzymes, vitamins, hair growth actives, sunscreens, and combinations thereof.

58. The composition of 54 wherein the skin active agent is a hair growth active selected from the group consisting of zinc lactobionate, zinc pyrithione, and combinations thereof.

59. The composition of claim 54 wherein the composition contains less than 2% by weight of a cleansing surfactant.

60. The composition of claim 54 wherein the moisturizing material is a humectant and represents from about 1% to about 10% by weight of the composition.

61. The composition of claim 60 wherein the humectant is selected from the group consisting of polypropylene glycol, polyethylene glycol, ethyl hexanediol, hexylene glycol, glycerin, propylene glycol, sorbitol, and combinations thereof.

\* \* \* \* \*